Nov. 12, 1974 W. A. WARRINER Plant Pat. 3,650
ROSE PLANT
Filed Aug. 9, 1973
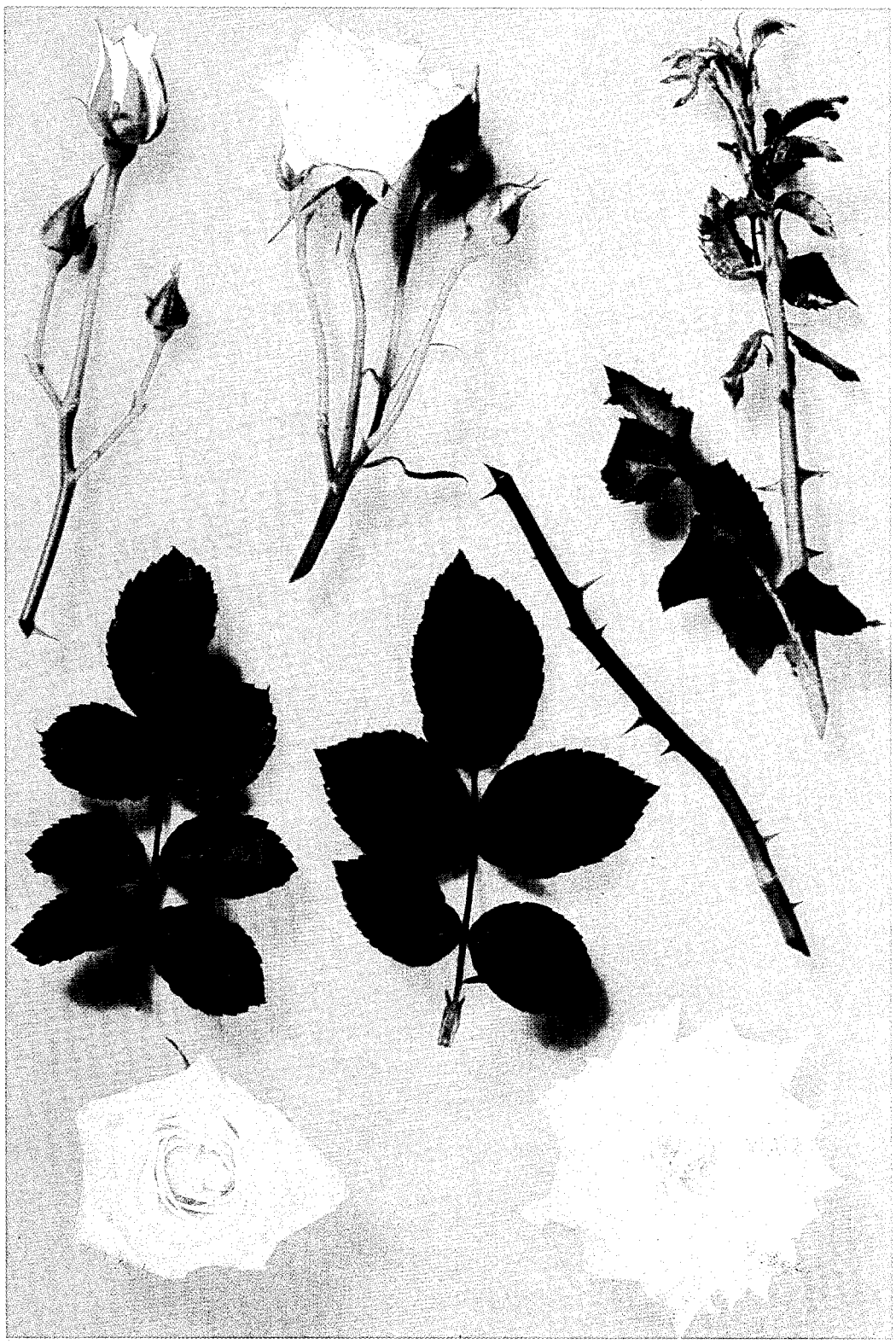

United States Patent Office

Plant Pat. 3,650
Patented Nov. 12, 1974

3,650
ROSE PLANT

William A. Warriner, Tustin, Calif., assignor to Jackson & Perkins Company, Medford, Oreg.

Filed Aug. 9, 1973, Ser. No. 387,190
Int. Cl. A01h *5/00*
U.S. Cl. Plt.—24 1 Claim

The present invention relates to a new cultivar of rose plant of the floribunda class which was originated by me by crossing the cultivar Yellow Pinocchio with pollen from a seedling of Rumba and Allgold.

The primary objective of this breeding was to produce a new yellow rose cultivar of the floribunda class, suitable for use as a greenhouse grown cut flower. This objective was substantially achieved as evidenced by the following unique combinations of characteristics which are outstanding in the new cultivar and which distinguish it from its parents as well as from all other cultivars of which I am aware.

1. A vigorous, well branched plant regrowing quickly after harvest of cut flowers.
2. Medium size buds developing into well sculptured open flowers which hold form and color very well when used as cut flowers.
3. Flower color near Lemon yellow from opening to fully open stages.
4. High rate of cut flower production of medium length stems.
5. Attractive dark green, semi-glossy foliage.

Asexual reproduction of this new cultivar by budding, as performed at Wasco, California, shows that the foregoing characteristics and distinctions come true to form and are established and transmitted through succeeding propagations.

The accompanying drawing shows typical specimens of the vegetative growth and flowers of this new cultivar in different stages of development, depicted in color as nearly true as it is reasonably possible to make the same in a color illustration of this character.

The following is a detailed description of my new rose variety with color terminology in accordance with *Wilson's Horticultural Color Chart,* except where ordinary dictionary significance of color is indicated.

Parentage: Seedling
- *Seed parent.*—Seedling of Yellow Pinocchio
- *Pollen parent.*—(Rumba×Allgold)

Classification:
- *Botanic.*—Rosa hybrid
- *Commercial.*—Floribunda.

FLOWER

Observations were made at Irvine, California, in mid-June, of greenhouse plants and flowers.

Blooming Habit: Recurrent—continuous.

Bud:
- *Size.*—one inch when petals start to unfurl.
- *Form.*—Blunt top, ovoid.
- *Color.*—When sepals first divide—Chrome Yellow (605) occasionally overlaid with Coral Pink (0619) near tips of outer petals. When half blown; inside of petals—near Lemon Yellow (4), reverse of petals—same.
- *Sepals.*—Color: Outer surface—near Scheeles Green (860/3) but lighter in center portion. Inner surface—much lighter than Scheeles Green (860/3). Three appendaged sepals heavily appendaged. Two unappendaged sepals glandular edged.
- *Receptacle.*—Color: Slightly lighter than Lettuce Green (861/3). Shape: Funnel. Size: Large. Surface: Smooth.
- *Peduncle.*—Length: Medium. Surface: Slightly prickly. Color: Lighter than Lettuce Green (861/3). Strength: Stiff, erect.
- *Opening.*—Petals roll back—very slightly pointed.

Bloom:
- *Size.*—Medium. Average size when fully expanded, 2½ inches.
- *Borne.*—Singly and several together.
- *Stems.*—Medium.
- *Form.*—When first open, high center. Permanence—retains its form to the end.
- *Petalage.*—Number of petals under normal conditions, 25–35.
- *Color.*—Center of flowers: Upper side of petals—Lemon Yellow (4). Reverse side of petals—Same. Outer petals: Upper side of petals—Near Straw Yellow (604/1). Reverse of petals—Same. General tonality from a distance—Lemon Yellow (4). No variegations.
- *Discoloration.*—General tonality at end of first day—Lemon Yellow (4). Third day—Begins to lighten to Straw Yellow (604/1). After 5–6 days color is mostly near Straw Yellow (604/2).
- *Fragrance.*—None.

Petals:
- *Texture.*—Thick.
- *Surface.*—Inside—satiny. Reverse—satiny.
- *Shape.*—Round.
- *Form.*—Tips slightly recurved.
- *Arrangement.*—Imbricated.
- *Petaloids in center.*—Few.
- *Persistence.*—Drop off cleanly.
- *Lastingness.*—On the plant—very long. As cut flower—very long.

Reproductive Parts:
- *Stamens, Anthers.*—Medium, many. Color—yellow.
- *Stamens, Filaments (threads).*—Medium. Color—yellow.
- *Pollen.*—Lemon yellow.
- *Stigmas.*—Color—Primrose Yellow (601/2).
- *Ovaries.*—All enclosed in calyx.

Fruit: (Not observed).

PLANT

Form: Bush.

Growth: Very vigorous, branching, compact.

Foilage: Number of leaflets on normal mid-stem leaves, 5, occasionally 7.
- *Size.*—Large.
- *Quantity.*—Normal.
- *Color.*—New foliage: Glossy surface, near Lettuce Green (861/3) overlaid heavily with Garnet Brown (00918/3)—Old foliage: Semi-glossy upper surface, darker than Parsley Green (00962).

Leaflets:
- *Shape.*—Oval.
- *Texture.*—Upper side—semi-glossy. Under side—smooth. Ribs and veins—ordinary.
- *Edge.*—Serrated.
- *Serration.*—Single, small.
- *Petiole.*—(rachis)—Color—Garnet Brown (00918/3) upper side, Lettuce Green (861/3) below. Underside—prickles.
- *Stipules.*—Long, serrated.
- *Disease Resistance.*—Resistant to mildew and blackspot, under normal growing conditions, at Irvine, California.

Wood:
- *New Wood.*—Color—light green. Bark—smooth.
- *Old Wood.*—Color—green. Bark—smooth.

Thorns:

*Quantity.*—On main stalks from base—ordinary. On laterals from stalk—ordinary.

*Form.*—Narrow base, long, straight.

*Color.*—Red.

Prickles:

*Quantity.*—On main stalks—none. On laterals—none.

Short Needles:

*Quantity.*—On main stalks—none. On laterals—none.

I claim:

1. A new and distinct cultivar of rose plant of the floribunda class, substantially as herein shown and described, characterized particularly as to novelty by the unique combination of its ovoid, chrome yellow bud, high centered Lemon yellow flower, dark semi-glossy foliage, and high rate of production of flowers borne mostly on stems of medium length.

No references cited.

ROBERT E. BAGWILL, Primary Examiner